United States Patent [19]
Chabot-Fletcher

[11] Patent Number: 5,952,483
[45] Date of Patent: Sep. 14, 1999

[54] HUMAN IκB-β

[75] Inventor: Marie C Chabot-Fletcher, Phoenixville, Pa.

[73] Assignee: SmithKline Beecham Corporation, Philadelphia, Pa.

[21] Appl. No.: 08/903,851

[22] Filed: Jul. 31, 1997

[51] Int. Cl.$^6$ .................................................. C07H 21/04
[52] U.S. Cl. ................... 536/23.5; 435/69.1; 435/252.3; 435/320.1; 435/325; 435/410
[58] Field of Search ........................ 536/23.5; 435/252.3, 435/325, 320.1, 6, 69.1, 410

[56] References Cited

U.S. PATENT DOCUMENTS 5,597,898  1/1997  Ghosh .

FOREIGN PATENT DOCUMENTS

WO 92/20795  11/1992  WIPO .

OTHER PUBLICATIONS

Thompson et al. Cell. vol. 80: 573–582, Feb. 1995.
Link et al J. B. C. vol. 267: 239–246, Jan. 1992.
Accession #L40407—Homo sapiens thyroid receptor interactor (TRIP9) gene, 1995.
Accession #U19799—Mus Musulus IkB–b, 1995.
Accession #I34460—NF–kappaB activation regulatory protein, IkappaB–beta, Jan. 1997.
HGS#1969886, Feb., 1997.
Thompson, J.E. et al., "IkB–b regulates the persistent response in a biphasic activation of NF–kB", *Cell* 80:573–582, 1995.
Lee, J.W. et al. "Two classes of proteins dependent on either the presence or absence of thyroid hormone for interaction with the thyroid hormone receptor", *Mol. Endocrinology* 9:243–254, 1995.
Zabel, U. et al. "Purified human IkB can rapidly dissociate the complex of the NF–kB transcription factor with its cognate DNA", *Cell* 61:255–265, 1990.
Chu, Z. et al. "Basal phosphorylation of the PEST domain in IkBb regulates its functional interaction with the c–rel proto–oncogene product", *Mol. Cell. Bio.* 16:5974–5984, 1996.

*Primary Examiner*—Christina Y. Chan
*Assistant Examiner*—Patrick J. Nolan
*Attorney, Agent, or Firm*—William T. Han; Ratner & Prestia; William T. King

[57] ABSTRACT

IκB-β polypeptides and polynucleotides and methods for producing such polypeptides by recombinant techniques are disclosed. Also disclosed are methods for utilizing IB-β polypeptides and polynucleotides in the design of protocols for the treatment of inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia, among others, and diagnostic assays for such conditions.

10 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1227 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
CGGGTCGACC CACGCGTCCG CCCAGCTACA GGCGGGCGAC TGCGGGGGGC CCCTGAGGCG      60

GCGGGGGCCA TGGCTGGGGT CGCGTGCTTG GGAAAAGCTG CCGACGCAGA TGAATGGTGC     120

GACAGCGGCC TGGGCTCCCT GGGTCCGGAC GCAGCGGCCC CCGGAGGACC TGGGTTGGGC     180

GCGGAGTTGG GCCCGGGGCT GTCGTGGGCT CCCCTCGTCT TCGGCTACGT CACTGAGGAT     240

GGGGACACGG CACTGCACTT GGCTGTGATT CATCAGCATG AACCCTTCCT GGATTTTCTT     300

CTAGGCTTCT CGGCCGGCAC TGAGTACATG GACCTGCAGA ATGACCTAGG CCAGACAGCC     360

CTGCACCTGG CAGCCATCCT GGGGGAGACA TCCACGGTGG AGAAGCTGTA CGCAGCAGGC     420

GCCGGGCTGT GTGTGGCGGA GCGTAGGGGC CACACGCGCG TGCACCTGGC CTGCCGTGTG     480

GGGGCACACG CCTGTGCCCG TGCCCTGCTT CAGCCCCGCC CCGGCGCCC CAGGGAAGCC     540

CCCGACACCT ACCTCGCTCA GGGCCCTGAC CGTACTCCCG ACACCAACCA TACCCCTGTC     600

GCCTTGTACC CCGATTCCGA CTTGGAGAAG GAAGAAGAGG AGAGTGAGGA GGACTGGAAG     660

CTGCAGCTGG AGGCTGAAAA CTACGAGGGC CACACCCCAC TCCACGTGGC CGTTATCCAC     720

AAAGATGTGG AGATGGTCCG GCTGCTCCGA GATGCTGGAG CTGACCTTGA CAAACCGGAG     780

CCCACGTGCG GCCGGAGCCC CCTTCATTTG GCAGTGGAGG CCCAGGCAGC CGATGTGCTG     840

GAGCTTCTCC TGAGGGCAGG CGCGAACCCT GCTGCCCGCA TGTACGGTGG CCGCACCCCA     900

CTCGGCAGTG CCATGCTCCG GCCCAACCCC ATCCTCGCCC GCCTCCTCCG TGCACACGGA     960

GCCCCTGAGC CCGAGGGCGA GGACGAGAAA TCCGGCCCCT GCAGCAGCAG TAGCGACAGC    1020

GACAGCGGAG ACGAGGGCGA TGAATACGAC GACATTGTGG TTCACAGCAG CCGCAGCCAA    1080

ACCCGGCTGC CTCCCACCCC AGCCTCAAAA CCTCTTCCTG ACGACCCCG CCCCGTGTGA    1140
```

```
TTTGTTTCAT TGTTAATATA ATTTCCAGTT TAATAAACAA AACCCTAGTT CTGACAACCA    1200

GGAAAAAAAA AAAAAAAAAA AAAAAAA                                       1227
```

(2) INFORMATION FOR SEQ ID NO:2:

(i) SEQUENCE CHARACTERISTICS:
        (A) LENGTH: 356 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Gly Val Ala Cys Leu Gly Lys Ala Ala Asp Ala Asp Glu Trp
 1               5                  10                  15

Cys Asp Ser Gly Leu Gly Ser Leu Gly Pro Asp Ala Ala Ala Pro Gly
                20                  25                  30

Gly Pro Gly Leu Gly Ala Glu Leu Gly Pro Gly Leu Ser Trp Ala Pro
            35                  40                  45

Leu Val Phe Gly Tyr Val Thr Glu Asp Gly Asp Thr Ala Leu His Leu
 50                  55                  60

Ala Val Ile His Gln His Glu Pro Phe Leu Asp Phe Leu Leu Gly Phe
65                  70                  75                  80

Ser Ala Gly Thr Glu Tyr Met Asp Leu Gln Asn Asp Leu Gly Gln Thr
                85                  90                  95

Ala Leu His Leu Ala Ala Ile Leu Gly Glu Thr Ser Thr Val Glu Lys
            100                 105                 110

Leu Tyr Ala Ala Gly Ala Gly Leu Cys Val Ala Glu Arg Arg Gly His
        115                 120                 125

Thr Ala Leu His Leu Ala Cys Arg Val Gly Ala His Ala Cys Ala Arg
130                 135                 140

Ala Leu Leu Gln Pro Arg Pro Arg Arg Pro Arg Glu Ala Pro Asp Thr
145                 150                 155                 160

Tyr Leu Ala Gln Gly Pro Asp Arg Thr Pro Asp Thr Asn His Thr Pro
                165                 170                 175

Val Ala Leu Tyr Pro Asp Ser Asp Leu Glu Lys Glu Glu Glu Glu Ser
            180                 185                 190

Glu Glu Asp Trp Lys Leu Gln Leu Glu Ala Glu Asn Tyr Glu Gly His
        195                 200                 205

Thr Pro Leu His Val Ala Val Ile His Lys Asp Val Glu Met Val Arg
210                 215                 220

Leu Leu Arg Asp Ala Gly Ala Asp Leu Asp Lys Pro Glu Pro Thr Cys
225                 230                 235                 240

Gly Arg Ser Pro Leu His Leu Ala Val Glu Ala Gln Ala Ala Asp Val
                245                 250                 255

Leu Glu Leu Leu Leu Arg Ala Gly Ala Asn Pro Ala Ala Arg Met Tyr
            260                 265                 270

Gly Gly Arg Thr Pro Leu Gly Ser Ala Met Leu Arg Pro Asn Pro Ile
        275                 280                 285

Leu Ala Arg Leu Leu Arg Ala His Gly Ala Pro Glu Pro Glu Gly Glu
290                 295                 300

Asp Glu Lys Ser Gly Pro Cys Ser Ser Ser Asp Ser Asp Ser Gly
305                 310                 315                 320

Asp Glu Gly Asp Glu Tyr Asp Asp Ile Val Val His Ser Ser Arg Ser
                325                 330                 335
```

```
Gln Thr Arg Leu Pro Pro Thr Pro Ala Ser Lys Pro Leu Pro Asp Asp
            340                 345                 350
Pro Arg Pro Val
        355
```

HUMAN IκB-β

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the IκB family, hereinafter referred to as IκB-β. The invention also relates to inhibiting or activating the action of such polynucleotides and polypeptides.

BACKGROUND OF THE INVENTION

The transcription factor NF-κB is key in regulating the expression of many genes involved in immune and inflammatory processes. In most cells NF-κB is present in the cytoplasm complexed with a member of the IκB family of proteins. IκB was originally identified as a labile factor which inhibited the activity of NF-κB by a directed protein-protein interaction. Two forms of the protein IκB-α and IκB-β, were purified from cytosolic fractions of human placenta (Zabel and Baeuerle, Cell 61:255–265, 1990) and at least three additional IκB family members have been described (Miyamoto and Verma, Adv. Cancer Res. 66:255–292, 1995). The activation of NF-κB upon cell activation is thought to involve the inducible phosphorylation of IκB family members on two N-terminal serines by a novel kinase prior to its degradation thereby allowing the free NF-κB to migrate to the nucleus where it binds to its consensus motif in target genes. Inhibition of either IκB phosphorylation or its degradation is known to inhibit the activation of NF-κB and thereby inhibit the expression of a number of immune and inflammatory mediators. This indicates that the IκB family has an established, proven history as therapeutic targets. Clearly there is a need for identification and characterization of further members of the IκB family which can play a role in preventing, ameliorating or correcting dysfunctions or diseases, including, but not limited to, inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia.

SUMMARY OF THE INVENTION

In one aspect, the invention relates to IκB-β polypeptides and recombinant materials and methods for their production. Another aspect of the invention relates to methods for using such IκB-β polypeptides and polynucleotides. Such uses include the treatment of inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia, among others. In still another aspect, the invention relates to methods to identify agonists and antagonists using the materials provided by the invention, and treating conditions associated with IκB-β imbalance with the identified compounds. Yet another aspect of the invention relates to diagnostic assays for detecting diseases associated with inappropriate IκB-β activity or levels.

DESCRIPTION OF THE INVENTION

Definitions

The following definitions are provided to facilitate understanding of certain terms used frequently herein.

"IκB-β" refers, among others, generally to a polypeptide having the amino acid sequence set forth in SEQ ID NO:2 or an allelic variant thereof.

"IκB-β activity or IκB-β polypeptide activity" or "biological activity of the IκB-β or IκB-β polypeptide" refers to the metabolic or physiologic function of said IκB-β including similar activities or improved activities or these activities with decreased undesirable side-effects. Also included are antigenic and immunogenic activities of said IκB-κ.

"IκB-β gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (*COMPUTATIONAL MOLECULAR BIOLOGY*, Lesk, A. M., ed., Oxford University Press, New York, 1988; *BIOCOMPUTING: INFORMATICS AND GENOME PROJECTS*, Smith, D. W., ed., Academic Press, New York, 1993; *COMPUTER ANALYSIS OF SEQUENCE DATA, PART I*, Griffin, A. M., and Griffin, H. G., eds., Humana Press, New Jersey, 1994; *SEQUENCE ANALYSIS IN MOLECULAR BIOLOGY*, von Heinje, G., Academic Press, 1987; and *SEQUENCE ANALYSIS PRIMER*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(l) :387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO:1 is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to IκB-β polypeptides (or IκB-β proteins). The IκB-β polypeptides include the polypeptide of SEQ ID NO:2; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO:2. Furthermore, those with at least 97–99% are highly preferred. Also included within IκB-β polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Furthermore, those with at least 97–99% are highly preferred. Preferably IκB-β polypeptide exhibit at least one biological activity of IκB-β.

The IκB-β polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the IκB-β polypeptides are also included in the invention. A fragment is a polypeptide having an amino acid sequence that entirely is the same as part, but not all, of the amino acid sequence of the aforementioned IκB-β polypeptides. As with IκB-β polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of IκB-β polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of IκB-β polypeptides, except for deletion of a continuous series of residues that includes the amino termiinus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate IκB-β activity, including those with a similar activity or an improved activity, or with a decreased undesirable activity. Also included are those that are antigenic or immunogenic in an animal, especially in a human.

Preferably, all of these polypeptide fragments retain the biological activity of the IκB-β, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The IκB-β polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to IκB-β polynucleotides. IκB-β polynucleotides include isolated polynucleotides which encode the IκB-β polypeptides and fragments, and polynucleotides closely related thereto. More specifically, IκB-β polynucleotide of the invention include a polynucleotide comprising the nucleotide sequence contained in SEQ ID NO:1 encoding a IκB-β polypeptide of SEQ ID NO:2, and polynucleotide having the particular sequence of SEQ ID NO:1. IκB-β polynucleotides further include a polynucleotide comprising a nucleotide sequence that has at least 80% identity over its entire length to a nucleotide sequence encoding the IκB-β polypeptide of SEQ ID NO:2, and a polynucleotide comprising a nucleotide sequence that is at least 80% identical to of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under IκB-β polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such IκB-β polynucleotides.

IκB-β of the invention is structurally related to other proteins of the IκB family, as shown by the results of sequencing the cDNA of Table 1 (SEQ ID NO:1) encoding human IκB-β. The cDNA sequence of SEQ ID NO:1 contains an open reading frame (nucleotide number 70 to 1140) encoding a polypeptide of 357 amino acids of SEQ ID NO:2. The amino acid sequence of Table 2 (SEQ ID NO:2) has about 96.15% identity (using GAP) in 357 amino acid residues with Trip9 (J. W. Lee et al., Mol. Endocrinol. 9:243–254, 1995). Furthermore, IκB-β (SEQ ID NO:2) is 84.3% identical to the murine IκB-β over 360 amino acid residues (Thompson et al., Cell 80:573–582, 1995). The nucleotide sequence of Table 1 (SEQ ID NO:1) has about 88.8% identity (using GAP) over 1227 nucleotide residues with Homo sapiens thyroid receptor interacting protein-9 (J. W. Lee et al., Mol. Endocrinol. 9:243–254, 1995). Furthermore, IκB-β (SEQ ID NO:1) is 80.2% identical to murine IκB-β over 1242 nucleotide base residues (Thompson J. E. et al., Cell 80:573–582, 1995) Thus IκB-β polypeptides and polynucleotides of the present invention are expected to have, inter alia, similar biological functions/properties to their homologous polypeptides and polynucleotides, and their utility is obvious to anyone skilled in the art.

TABLE 1[a]

CGGGTCGACCCACGCGTCCGCCCAGCTACAGGCGGGCGACTGCGGGGGGCCCCTGAGGCGGCGGGGGCC

ATGGCTGGGGTCGCGTGCTTGGGAAAAGCTGCCGACGCAGATGAATGGTGCGACAGCGGCCTGGGCTCC

CTGGGTCCGGACGCAGCGGCCCCCGGAGGACCTGGGTTGGGCGCGGAGTTGGGCCCGGGGCTGTCGTGG

GCTCCCCTCGTCTTCGGCTACGTCACTGAGGATGGGGACACGGCACTGCACTTGGCTGTGATTCATCAG

CATGAACCCTTCCTGGATTTTCTTCTAGGCTTCTCGGCCGGCACTGAGTACATGGACCTGCAGAATGAC

CTAGGCCAGACAGCCCTGCACCTGGCAGCCATCCTGGGGGAGACATCCACGGTGGAGAAGCTGTACGCA

GCAGGCGCCGGGCTGTGTGTGGCGGAGCGTAGGGGCCACACGGCGCTGCACCTGGCCTGCCGTGTGGGG

GCACACGCCTGTGCCCGTGCCCTGCTTCAGCCCCGCCCCGGCGCCCAGGGAAGCCCCCGACACCTAC

CTCGCTCAGGGCCCTGACCGTACTCCCGACACCAACCATACCCCTGTCGCCTTGTACCCCGATTCCGAC

TTGGAGAAGGAAGAAGAGGAGAGTGAGGAGGACTGGAAGCTGCAGCTGGAGGCTGAAAACTACGAGGGC

CACACCCCACTCCACGTGGCCGTTATCCACAAAGATGTGGAGATGGTCCGGCTGCTCCGAGATGCTGGA

GCTGACCTTGACAAACCGGAGCCCACGTGCGGCCGGAGCCCCCTTCATTTGGCAGTGGAGGCCCAGGCA

GCCGATGTGCTGGAGCTTCTCCTGAGGGCAGGCGCGAACCCTGCTGCCCGCATGTACGGTGGCCGCACC

CCACTCGGCAGTGCCATGCTCCGGCCCAACCCCATCCTCGCCCGCCTCCTCCGTGCACACGGAGCCCCT

GAGCCCGAGGGCGAGGACGAGAAATCCGGCCCCTGCAGCAGCAGTAGCGACAGCGACAGCGGAGACGAG

GGCGATGAATACGACGACATTGTGGTTCACAGCAGCCGCAGCCAAACCCGGCTGCCTCCCACCCCAGCC

TCAAAACCTCTTCCTGACGACCCCCGCCCCGTGTGATTTGTTTCATTGTTAATATAATTTCCAGTTTAA

TAAACAAAACCCTAGTTCTGACAACCAGGAAAAAAAAAAAAAAAAAAAAAAAAAA

[a] A nucleotide sequence of a human IκB-β (SEQ ID NO: 1).

TABLE 2[b]

MAGVACLGKAADADEWCDSGLGSLGPDAAAPGGPGLGAELGPGLSWAPLVFGYVTEDGDTALHLAVIHQ

HEPFLDFLLGFSAGTEYMDLQNDLGQTALHLAAILGETSTVEKLYAAGAGLCVAERRGHTALHLACRVG

AHACARALLQPRPRRPREAPDTYLAQGPDRTPDTNHTPVALYPDSDLEKEEEESEEDWKLQLEAENYEG

HTPLHVAVIHKDVEMVRLLRDAGADLDKPEPTCGRSPLHLAVEAQAADVLELLLRAGANPAARMYGGRT

PLGSAMLRPNPILARLLRAHGAPEPEGEDEKSGPCSSSSDSDSGDEGDEYDDIVVHSSRSQTRLPPTPA

SKPLPDDPRPV.

[b] An amino acid sequence of a human IκB-β (SEQ ID NO: 2).

One polynucleotide of the present invention encoding IκB-β may be obtained using standard cloning and screening, from a cDNA library derived from mRNA in cells of human hippocampus, synovial sarcoma, T lymphocytes, neutrophils, and pancreatic islet using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding IκB-β polypeptide of SEQ ID NO:2 may be identical to the polypeptide encoding sequence contained in Table 1 (nucleotide number 70 to 1140 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of IκB-β polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or preproprotein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci* USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding IκB-β variants comprise the ammo acid sequence IκB-β polypeptide of Table 2 (SEQ ID NO:2) in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full-length cDNAs and genomic clones encoding IκB-β polypeptide and to isolate cDNA and genomic clones of other genes (including genes encoding homologs and orthologs from species other than human) that have a high sequence similarity to the IκB-β gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding IκB-β polypeptide, including homologs and orthologs from species other than human, comprises the steps of screening an appropriate library under stringent hybridization conditions with a labeled probe having the SEQ ID NO:1 or a fragment thereof, and isolating full-length cDNA and genomic clones containing said polynucleotide sequence. Thus in another aspect, IκB-β polynucleotides of the present invention further include a nucleotide sequence comprising a nucleotide sequence that hybridize under stringent condition to a nucleotide sequence having SEQ ID NO:1 or a fragment thereof. Also included with IκB-β polypeptides are polypeptide comprising amino acid sequence encoded by nucleotide sequence obtained by the above hybridization condition. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA, followed by washing the filters in 0.1× SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic Lipid-mediated transfection, electroporation, transduction, scrape loading, ballistic introduction or infection.

Representative examples of appropriate hosts include bacterial cells, such as streptococci, staphylococci, *E. coli, Streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the IκB-β polypeptide is to be expressed for use in screening assays, generally, it is preferred that the polypeptide be produced at the surface of the cell. In this event, the cells may be harvested prior to use in the screening assay. If IκB-β polypeptide is secreted into the medium, the medium can be recovered in order to recover and purify the polypeptide; if produced intracellularly, the cells must first be lysed before the polypeptide is recovered.

IκB-β polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of IκB-β polynucleotides for use as diagnostic reagents. Detection of a mutated form of IκB-β gene associated with a dysfunction will provide a diagnostic tool that can add to or define a diagnosis of a disease or susceptibility to a disease which results from under-expression, over-expression or altered expression of IκB-β. Individuals carrying mutations in the IκB-β gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled IκB-β nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85: 4397–4401. In another embodiment, an array of oligonucleotides probes comprising IκB-β nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M.Chee et al., Science, Vol 274, pp 610–613 (1996)).

The diagnostic assays offer a process for diagnosing or determining a susceptibility to inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia through detection of mutation in the IκB-β gene by the methods described.

In addition, inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia, can be diagnosed by methods comprising determining from a sample derived from a subject an abnormally decreased or increased level of IκB-β polypeptide or IκB-β mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an IκB-β polypeptide, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia, which comprises:

(a) a IκB-β polynucleotide, preferably the nucleotide sequence of SEQ ID NO:1, or a fragment thereof;

(b) a nucleotide sequence complementary to that of (a);

(c) a IκB-β polypeptide, preferably the polypeptide of SEQ ID NO:2, or a fragment thereof, or (d) an antibody to a IκB-β polypeptide, preferably to the polypeptide of SEQ ID NO:2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative a gent of the disease.

Antibodies

The polypeptides of the invention or their fragments or analogs thereof, or cells expressing them can also be used as immunogens to produce antibodies inmunospecific for the IκB-β polypeptides. The term "immunospecific" means that the antibodies have substantial greater affinity for the polypeptides of the invention than their affinity for other related polypeptides in the prior art.

Antibodies generated against the IκB-β polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoata technique Kohler, G. and Milstein, C., *Nature* (1975) 256:495–497), the trioma technique, the human B-cell hybridoma technique (Kozbor et al., *Immunology Today* (1983) 4:72) and the EBV-hybridonma technique (Cole et al., *MONOCLONAL ANTIBODIES AND CANCER THERAPY,* pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against IκB-β polypeptides may also be employed to treat inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia, among others.

Vaccines

Another aspect of the invention relates to a method for inducing an immunological response in a manual which comprises inoculating the mammal with IκB-β polypeptide, or a fragment thereof, adequate to produce antibody and/or T cell immune response to protect said animal from inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia, among others. Yet another aspect of the invention relates to a method of inducing immunological response in a mammal which comprises, delivering IκB-β polypeptide via a vector directing expression of IκB-β polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a IκB-β polypeptide wherein the composition comprises a IκB-β polypeptide or IκB-β gene. The vaccine formulation may further comprise a suitable carrier. Since IκB-β polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freezedried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The IκB-β polypeptide of the present invention may be employed in a screening process for compounds which activate (agonists) or inhibit activation of (antagonists, or otherwise called inhibitors) the IκB-β polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, receptors, enzymes, etc., as the case may be, of the polypeptide of the present invention; or may be structural or functional mimetics of the polypeptide of the present invention. See Coligan et al., *Current Protocols in Immunology* 1(2):Chapter 5 (1991).

IκB-β polypeptides are responsible for many biological functions, including many pathologies. Accordingly, it is desirous to find compounds and drugs which stimulate IκB-β polypeptide on the one hand and which can inhibit the function of IκB-β polypeptide on the other hand. In general, agonists are employed for therapeutic and prophylactic purposes for such conditions as inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia. Antagonists may be employed for a variety of therapeutic and prophylactic purposes for such conditions as inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia.

In general, such screening procedures may involve using appropriate cells which express the IκB-β polypeptide or respond to IκB-β polypeptide of the present invention. Such cells include cells from mammals, yeast, Drosophila or *E. coli*. Cells which express the IκB-β polypeptide (or cell membrane containing the expressed polypeptide) or respond to IκB-β polypeptide are then contacted with a test compound to observe binding, or stimulation or inhibition of a functional response. The ability of the cells which were contacted with the candidate compounds is compared with the same cells which were not contacted for IκB-β activity.

The assays may simply test binding of a candidate compound wherein adherence to the cells bearing the IκB-β polypeptide is detected by means of a label directly or indirectly associated with the candidate compound or in an assay involving competition with a labeled competitor. Further, these assays may test whether the candidate compound results in a signal generated by activation of the IκB-β polypeptide, using detection systems appropriate to the cells bearing the IκB-β polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a IκB-β polypeptide to form a mixture, measuring IκB-β activity in the mixture, and comparing the IκB-β activity of the mixture to a standard.

The IκB-β cDNA, protein and antibodies to the protein may also be used to configure assays for detecting the effect of added compounds on the production of IκB-β MRNA and protein in cells. For example, an ELISA may be constructed for measuring secreted or cell associated levels of IκB-β protein using monoclonal and polyclonal antibodies by standard methods known in the art, and this can be used to discover agents which may inhibit or enhance the production of IκB-β (also called antagonist or agonist, respectively) from suitably manipulated cells or tissues.

The IκB-β protein may be used to identify membrane bound or soluble receptors, if any, through standard receptor binding techniques known in the art. These include, but are not limited to, ligand binding and crosslinking assays in which the IκB-β is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of IκB-β which compete with the binding of IκB-β to its receptors, if any. Standard methods for conducting screening assays are well understood in the art.

Examples of potential IκB-β polypeptide antagonists include antibodies or, in some cases, oligonucleotides or proteins which are closely related to the ligands, substrates, receptors, enzymes, etc., as the case may be, of the IκB-β polypeptide, e.g., a fragment of the ligands, substrates, receptors, enzymes, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for IκB-β polypeptides; or compounds which decrease or enhance the production of IκB-β polypeptides, which comprises:

(a) a IκB-β polypeptide, preferably that of SEQ ID NO:2;

(b) a recombinant cell expressing a IκB-β polypeptide, preferably that of SEQ ID NO:2;

(c) a cell membrane expressing a IκB-β polypeptide; preferably that of SEQ ID NO:2; or (d) antibody to a IκB-β polypeptide, preferably that of SEQ ID NO:2.

It will be appreciated that in any such kit, (a), (b), (c) or (d) may comprise a substantial component.

Prophylactic and Therapeutic Methods

This invention provides methods of treating abnormal conditions such as, inflammatory conditions including but not limited to rheumatoid arthritis, dermatosis (eg. psoriasis), inflammatory bowel disease, autoimmune diseases, tissue and/or organ rejection, Alzheimer's disease, stroke, atherosclerosis, restenosis, cancer, viral infection including but not limited to AIDS, osteoarthritis, osteoperosis, and Ataxia Telangiestasia, related to both an excess of and insufficient amounts of IκB-β polypeptide activity.

If the activity of IκB-β polypeptide is in excess, several approaches are available. One approach comprises administering to a subject an inhibitor compound (antagonist) as hereinabove described along with a pharmaceutically acceptable carrier in an amount effective to inhibit the function of the IκB-β polypeptide, such as, for example, by blocking the binding of ligands, substrates, receptors, enzymes, etc., or by inhibiting a second signal, and thereby alleviating the abnormal condition. In another approach, soluble forms of IκB-β polypeptides still capable of binding the ligand, substrate, enzymes, receptors, etc. in competition with endogenous IκB-β polypeptide may be administered. Typical embodiments of such competitors comprise fragments of the IκB-β polypeptide.

In still another approach, expression of the gene encoding endogenous IκB-β polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression,* CRC Press, Boca Raton, Fla. (1988). Alternatively, oligonucleotides which form triple helices with the gene can be supplied. See, for example, Lee et al, *Nucleic Acids Res* (1979) 6:3073; Cooney et al., *Science* (1988) 241:456; Dervanetal., *Science* (1991) 251:1360. These oligomers can be administered per se or the relevant oligomers can be expressed in vivo.

For treating abnormal conditions related to an underexpression of IκB-β and its activity, several approaches are also available. One approach comprises administering to a subject a therapeutically effective amount of a compound which activates IκB-β polypeptide, i.e., an agonist as described above, in combination with a pharmaceutically acceptable carrier, to thereby alleviate the abnormal condition. Alternatively, gene therapy may be employed to effect the endogenous production of IκB-β by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd (1996). Another approach is to administer a therapeutic amount of IκB-β polypeptides in combination with a suitable pharmaceutical carrier.

Formulation and Administration

Peptides, such as the soluble form of IκB-β polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection.

Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

The gene expression profile of a variety of human tissues and cells, as determined by random sequencing of cDNA libraries, was searched for an expressed sequence tag (EST) with homology to the murine cDNA using the FASTA algorithm of the University of Wisconsin GCG software package. This comparison yielded several gene "hits". Chain termination sequencing was carried out on the full length clone using primers selected to permit overlapping bidirectional sequencing of the entire cDNA clone.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence that encodes the polypeptide of SEQ ID NO:2; or a nucleotide sequence which is fully complementary to said isolated polynucleotide.

2. An isolated polynucleotide comprising the polynucleotide sequence set forth in SEQ ID NO:1.

3. The isolated polynucleotide of claim 1 which is DNA or RNA.

4. An expression system comprising an isolated DNA or RNA molecule, wherein said expression system produces a IκB-β polypeptide comprising an amino acid sequence as set forth in SEQ ID NO:2 when said expression system is present in a compatible host cell.

5. An isolated host cell comprising the expression system of claim 4.

6. A process for producing a IκB-β polypeptide comprising culturing a host cell of claim 5 under conditions sufficient for the production of said polypeptide and recovering the polypeptide from the culture.

7. A process for producing a cell which produces a IκB-β polypeptide thereof comprising transforming or transfecting a host cell with the expression system of claim 4 such that the host cell, under appropriate culture conditions, produces a IκB-β polypeptide.

8. A recombinant host cell produced by the process of claim 7 expressing a IκB-β polypeptide.

9. The isolated polynucleotide of claim 1 wherein said nucleotide sequence is the entire length of the RNA transcript of SEQ ID NO:1; or a nucleotide sequence which is fully complementary to said isolated polynucleotide.

10. The isolated polynucleotide of claim 1 wherein said nucleotide sequence is the coding region of the RNA transcript of SEQ ID NO:1; or a nucleotide sequence which is fully complementary to said isolated polynucleotide.

* * * * *